United States Patent [19]

Milan et al.

[11] 4,054,127

[45] * Oct. 18, 1977

[54] ENDOMETRIAL SAMPLING INSTRUMENT

[76] Inventors: Albert R. Milan, 1335 Heather Road, Baltimore, Md. 21239; Raymond L. Markley, 707 Thornwood Court, Baltimore, Md. 21204

[ * ] Notice: The portion of the term of this patent subsequent to Mar. 23, 1993, has been disclaimed.

[21] Appl. No.: 618,365

[22] Filed: Oct. 1, 1975

Related U.S. Application Data

[63] Continuation-in-part of Ser. No. 505,709, Sept. 13, 1974, Pat. No. 3,945,372, which is a continuation of Ser. No. 365,850, June 1, 1973, abandoned.

[51] Int. Cl.² ............................................. A61B 10/00
[52] U.S. Cl. ....................................... 128/2 B; 128/304
[58] Field of Search ............... 128/2 B, 2 W, 2 R, 304

[56] References Cited

U.S. PATENT DOCUMENTS

| 584,407 | 6/1897 | Saint Cyr, Jr. | 128/304 |
|---|---|---|---|
| 626,625 | 6/1899 | May | 128/304 |
| 667,726 | 2/1901 | McDade | 128/304 |
| 865,571 | 9/1907 | Currey | 128/304 |
| 2,955,592 | 10/1962 | MacLean | 128/2 B |
| 3,592,186 | 7/1971 | Oster | 128/304 X |
| 3,732,858 | 5/1973 | Banko | 128/2 B |
| 3,796,211 | 3/1974 | Kohl | 128/2 B |
| D. 210,757 | 4/1968 | Michel | D83/12 |

*Primary Examiner*—Kyle L. Howell
*Attorney, Agent, or Firm*—Walter G. Finch

[57] ABSTRACT

An endometrial tissue-obtaining instrument includes a curved spiral section formed at one end of a flat plastic member and a handle portion at the other end. The spiral section is insertable into the endometrial cavity of a female patient and rotated by the handle portion to remove endometrial tissue from the wall thereof. The spiral section is withdrawn with the specimen of tissue.

10 Claims, 15 Drawing Figures

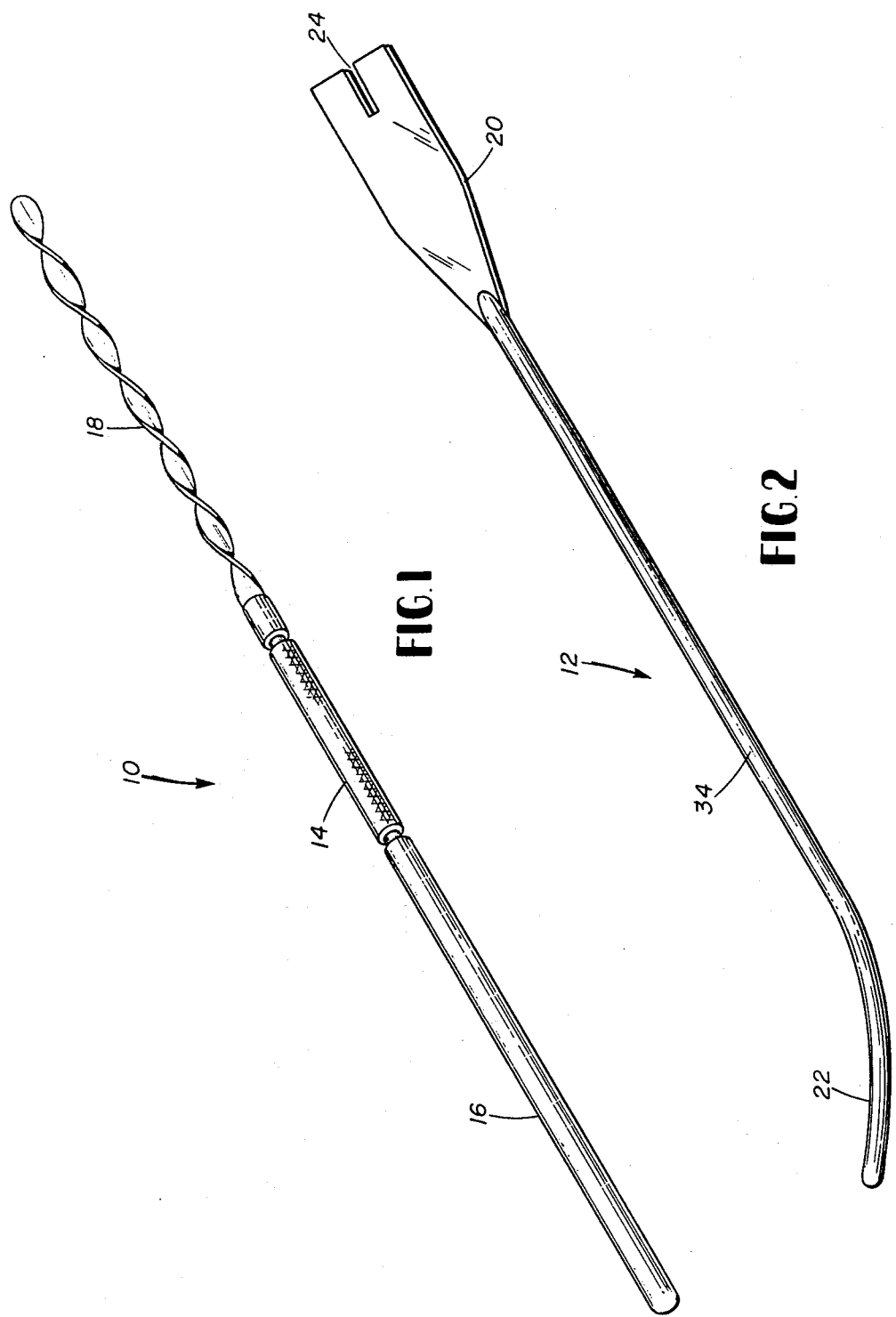

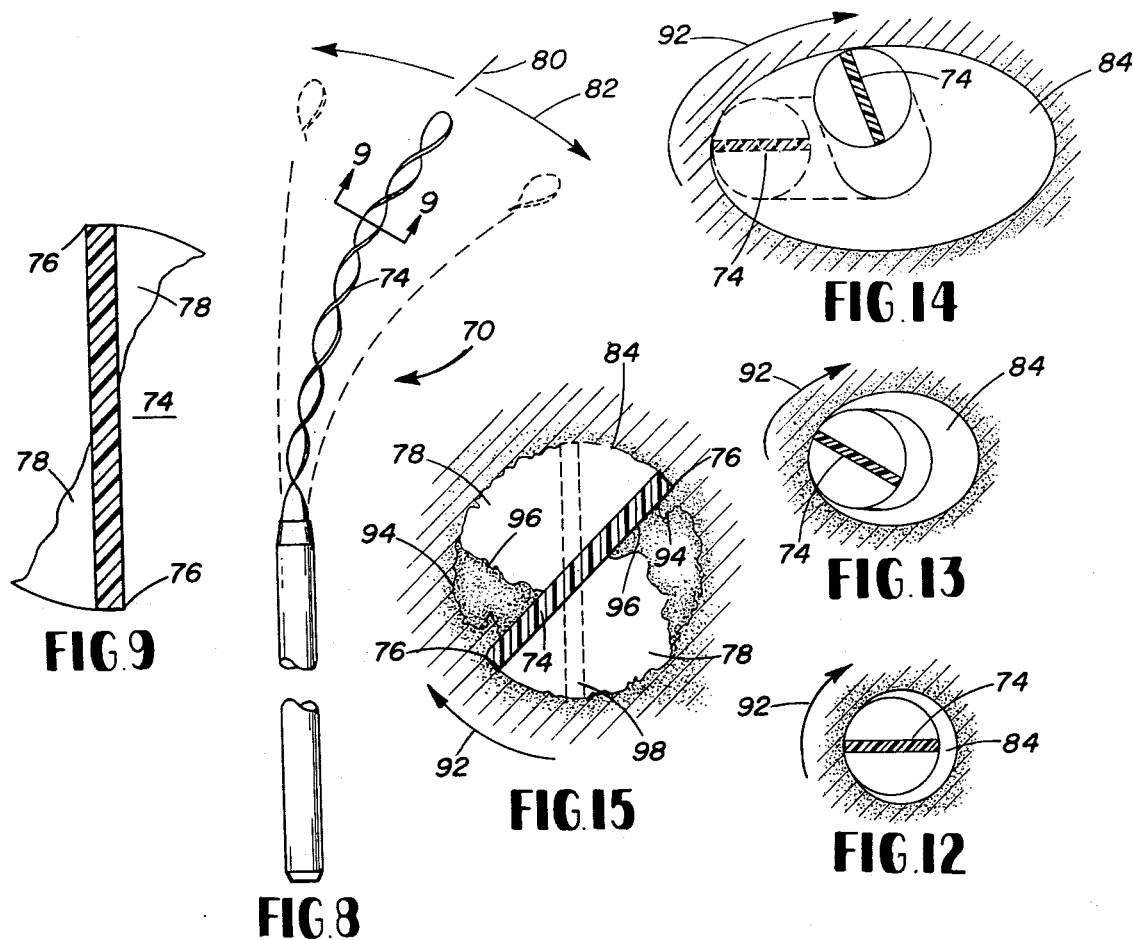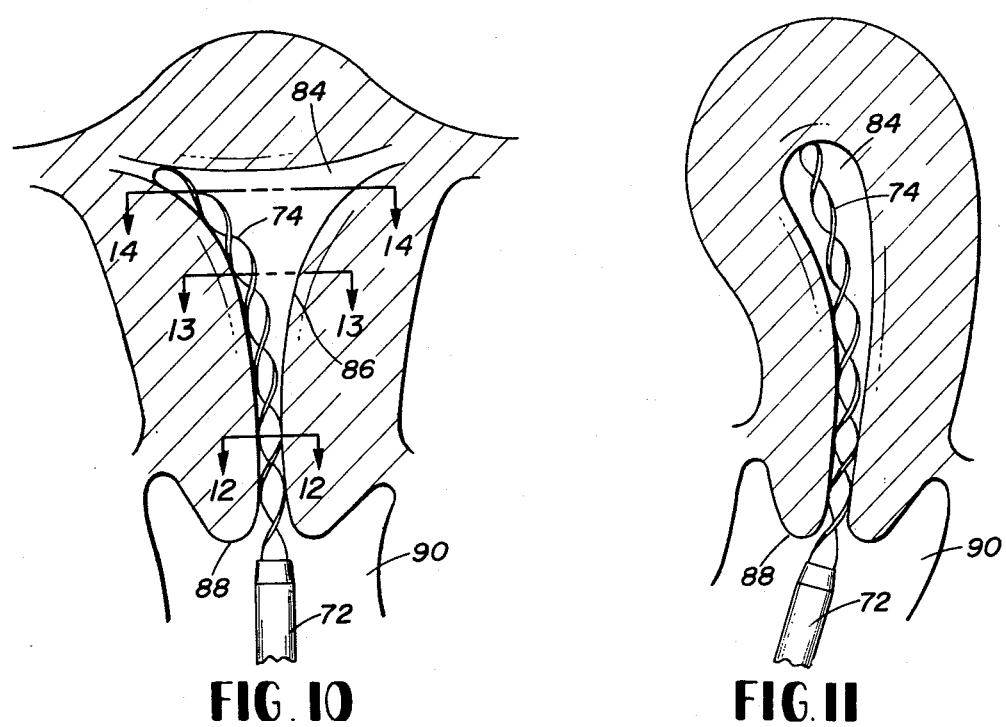

ENDOMETRIAL SAMPLING INSTRUMENT

CROSS-REFERENCE TO RELATED APPLICATIONS

The present application is a continuation-in-part of U.S. patent application Ser. No. 505,709, filed Sept. 13, 1974, now U.S. Pat. No. 3,945,372 which application was a continuation of now abandoned U.S. Pat. application Ser. No. 365,850, filed June 1, 1973.

BACKGROUND OF THE INVENTION

A. Field of the Invention

The invention relates to apparatus for obtaining tissue samples from body cavities of animals, particularly from the endometrial cavity of a human female.

B. Description of the Prior Art

In the routine cytopathological evaluation of the cervical-vaginal smear, the endocervical and endometrical components of the smear comprise a very small portion of the slide or may even be completely absent. Since post-menopausal mucous is usually very thick, tenacious, and essentially seals the endocervical canal, it is very difficult, and in many instances virtually impossible, for the efoliated endometrial cells to reach the vaginal pool. Consequently, these cells are rarely available in sufficient content when conducting a routine cervical-vaginal smear evaluation. The cervical-vaginal smear is a screening device for the detection of cervical cancer (neoplasia) or other hormonal changes.

Several techniques exist for the withdrawal of endometrial tissue for diagnosing endometrial neoplasia. However, these have proven to be complex, time consuming or have been of questionable diagnostic value. Some of these techniques have been acceptable by patients. However, the techniques are complex, unreliable, and expensive. Some examples of these techniques are commonly referred to as brush techniques, aspiration techniques, and jet washing techniques. Most of these techniques depend upon suspension of the obtained specimen of endometrial mucous and cells in a solution to dissolve or separate unwanted substances and subsequently separating the cells from the solution by centrifugation or filtration which results in the production of artifacts and a loss of a portion of the specimen. Paraffin embedding is then required, followed by the study of the resulting serial histological sections.

In the brush technique a brush, having bristles extending radially from a central support, is inserted into the womb to engage the endometrial tissue. When the brush is withdrawn, tissue clings to the brush. Thereafter, the brush, with tissue clinging thereto, must be placed in a solution to dissolve the bristles thereby leaving the tissue in solution. A centrifugal, or filtering, process follows to separate the tissue from the solution. The tissue can then be analyzed. The brush technique is time consuming and requires that each brush be dissolved which is costly. Also, the time delay between extraction of the tissue from the endometrial cavity and ultimate analysis thereof results in some loss in integrity of the tissue. This could provide less than desirable results in the ultimate tests.

In the jet washing technique, a saline solution is placed in a container, such as a syringe, which is inserted into the cavity. A vacuum reaction results as a suction is produced to suck the saline into the uterine cavity, thereby removing the mucous and exfoliated cells with the washing solution. Since the cells must remain in this solution for variable periods of time, and the solution may not be isotomic, the cells may shrink, or swell producing undesirable artifacts. This methods depends on an airtight system which is not always possible and therefore the entire collecting procedure may fail because no tissue is obtained.

Another technique involves the use of a curette which is inserted into the cavity to draw a sample of tissue from one area of the wall of said cavity. This curette technique does not provide a single sampling of tissue from essentially all areas of the womb and is thereby limiting in its resultant effectiveness. Several samples must be taken from a single patient to obtain a reasonable cross section of the endometrial tissue which lines all areas of the wall of the cavity. Even after all of this is done, there is no absolute assurance that sample tissue has been taken from all areas. This technique can be improved upon if there is a homogenous sampling of the entire surface of the uterine cavity. This technique is usually a hospital procedure and requires anesthesia because it is quite painful. Curettings are limited to histological study and do not adapt to office cytological screenings.

It becomes readily apparent, then, that the preparation, screening and final interpretation of these sections, obtained by presently available techniques, can be costly in terms of time and money. Further the material to be examined ultimately may be questionable in quality and inadequate for meaningful analysis. If the material is not processsed immediately, it becomes pale and washed out. Also, nuclear details are lost and osmotic artifacts may occur. Thus, better-than-average skill is required to prepare readable slides and the cytologist must be deft at differentiating between artifact and real pathology.

In the light of the foregoing, there has existed a dire need for a technique which facilitates direct smearing of the endometrial mucous from the withdrawal instrument onto a slide with rapid fixation to prevent drying and osmotic artifacts. Such a technique would desirably provide a good cross section of the endometrial flora secured on a single slide. This technique would thereby provide a thorough sampling of endometrial tissue from essentially all areas of the wall of the womb and result in a complete examination thereof which is fast and economical.

SUMMARY OF THE INVENTION

The present invention provides a tissue-obtaining instrument which is particularly suited for obtaining a tissue sample from the endometrial cavity of a female patient which sample is representative of the full surface area of the cavity. The present apparatus or instrument comprises a handle member terminating in a spiral member having straight sides and a curving longitudinal axis which generally conforms to the shape of the endometrial cavity. The spiral member is rounded at its outer end for patient comfort and is flexible in order to maximize contact with the surfaces of the cavity. The spiral member is insertable into the endometrial cavity of a female patient and rotated by manipulation of the handle member. The inherent springingness of the spiral member causes it to adapt itself to the different configurations of the walls of the cavity, thereby scraping mucous, cells, and tissue fragments from the walls of the cavity as it is continuously rotated. The lateral edges of the spiral are sharp and are capable of shearing off tissue fragments of the endometrial lining tissue which is incorporated into the specimen.

The spiral member is then withdrawn from the cavity with the tissue specimen clinging to the matte surface of the instrument and filling up the flutes of the spiral with the obtained specimens. The base of the spiral is then inserted into a slot of a plastic paddle. The spiral member is then pulled through the slot and is thereby caused to rotate through the slot, the tissue specimen being wiped from the surface of the spiral member or movement of said spiral member through the slot. The tissue thus deposited on the plastic paddle is then smeared onto a slide for immediate study or stored for future analysis. The use of this instrument in pregnancy may result in the dislodgement of the early implantation of an embryo. Its use in pregnancy is not recommended unless one is desirous of producing an early abortion.

It is an object of this invention, therefore, to provide a tissue sampling instrument for obtaining a tissue specimen from body cavities, particularly the endometrial cavity, which is representative of essentially an entire cross section of the tissues on the surface of the cavity.

Another object of this invention is to provide a medical instrument, and method of use thereof, which will permit the obtaining and withdrawal of endometrial tissue from the endometrial cavity in a form which is uncontaminated by other substances, and one which has inherent memory and inherent springingness.

Still another object of this invention is to provide a medical instrument which facilitates direct smearing of endometrial tissue as obtained from the instrument onto a slide with rapid fixation to prevent drying and osmotic artifacts, and the loss of cells critically needed to make an accurate diagnosis.

A further object of this invention is to provide a medical instrument for obtaining and analyzing endometrial tissue relatively quickly and less costly.

Still another object of this invention is to provide a medical instrument which permits the uncontaminated withdrawal of endometrial tissue from the womb by the instrument and transfer thereof to a separate implement for immediate transfer to an examination surface.

Yet another object is the provision of a medical instrument for withdrawal of endometrial tissue from the endometrial cavity of a patient in a relatively simple and efficient manner and in a nearly pain-free, routine, gynecological-office procedure, yielding a simple method for mass screening of large numbers of people.

Other objects and attendant advantages of this invention will become more readily apparent and understood from the following detailed description of the preferred embodiments thereof.

BRIEF DESCRIPTION OF THE DRAWINGS

FIG. 1 is a perspective of a medical instrument having a spiral end section embodying certain principles of the invention;

FIG. 2 is a perspective of an implement used with the medical instrument of FIG. 1 in accordance with certain principles of the invention;

FIG. 8 is a perspective of a second embodiment of the invention wherein the spiral end section is curved and has inherent ductility;

FIG. 9 is a section taken along line 9—9 of FIG. 8 emphasizing the sharp 90° edge of the spiral;

FIG. 10 is an elevation in partial section of the instrument being inserted into the endometrial cavity, wherein the curvature of the spiral end section causes contact thereof with essentially the full surface area of the cavity;

FIG. 11 is a side elevation of the instrument in use in the manner of FIG. 10;

FIG. 12 is a section taken along line 12—12 of FIG. 10;

FIG. 13 is a section taken along line 13—13 of FIG. 10;

FIG. 14 is a section taken along line 14—14 of FIG. 10; and

FIG. 15 is a section taken through the endometrial cavity illustrating the scraping action of the present invention.

DESCRIPTION OF THE PREFERRED EMBODIMENTS

Figure 3:
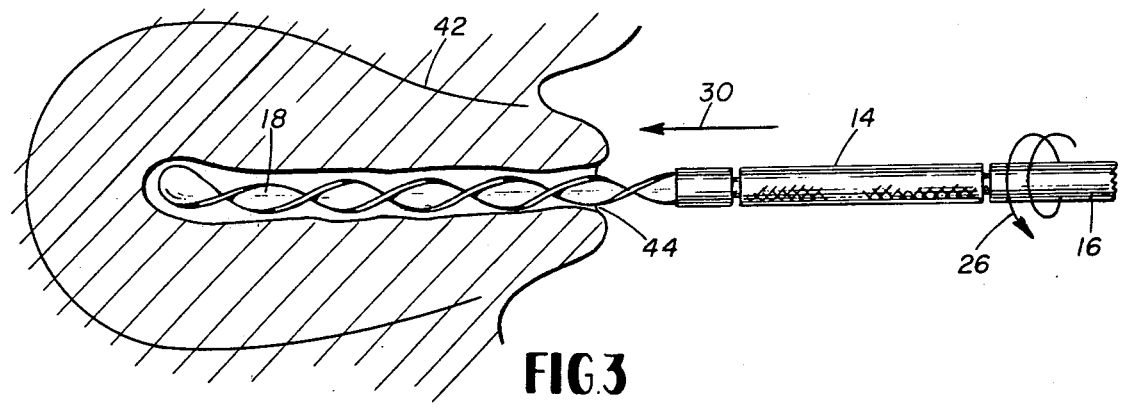
FIG. 3 is an elevation, in partial section, showing the spiral end section of the instrument of FIG. 1 being inserted into the endometrial cavity of a female patient.

Referring to FIG. 1, the invention is seen to comprise a medical instrument 10, of the nature of a cytology curette device, which is formed with a spiral end section 18. The spiral end section 18 has the appearance of having been formed from a flat piece of material which has been twisted about its longitudinal axis. A rotatable sleeve 14 is used to connect a handle 16, in essentially axial alignment in this embodiment of the invention, with the spiral section 18. The sleeve 14 could be connected to handle 16 and spiral section 18 by force fit or by means of a threaded connection. This permits ready handling of the spiral section 18 without the necessity of direct contact after assembly with the sleeve 12 and handle 16. The instrument 10 could be formed from a single piece of material with one end forming the spiral and the remaining or trailing portion forming the handle. The spiral section 18 is composed of any suitable inert plastic material which is resilient, tough and pliable. The surface of the spiral section 18 is sand blasted or otherwise treated to produce a matte or roughened surface. Additionally, the edges of the spiral section 18 are formed by the essentially 90° juncture of the side walls thereof and the longitudinal axis may be curved as will be fully described hereinafter. The edge of the section 18 are effectively sharp. Subsequent to manufacture, the spiral section 18 is sterilized and packaged for shipment and handling, prior to use, without concern for contamination.

The instrument 10 is used with an implement 12, shown in FIG. 2 which has a flat paddle 20 formed at one end and a curved portion 22 at the other end with an intermediate handle portion 34. The paddle 20 is formed with a slot 24. The width of the slot 24 is substantially equal to the thickness dimension of a flat portion of the spiral section 18 (FIG. 1). The opposing, longitudinal edges of the slot 24 are thinned so that the edges have a flexible wiper effect. The paddle 20 is also composed of an inert plastic material which is resilient, tough and pliable.

In use, the curved portion 22 of the implement 12 can be used to dilate the cervix, if needed, so that the instrument 10 can be moved in the direction of the arrow 30 where the spiral section 18 enters the womb 42 of a female patient through the entrance 44, and is thereby positioned within the endometrial cavity thereof. As noted, the long axis of the spiral section 18 is designed with a slight curvature to facilitate passage of the section beyond the internal opening of the cervix. The leading end of the spiral section 18 is rounded to minimize any pain to the patient during insertion. Thereafter, the instrument 10 is rotated, as indicated by arrow 26, for example, for six to ten turns. The rotating spiral section 18 gathers in the tissue-containing mucous aggregate 28 (FIG. 4) from the walls of the womb 42.

Figure 4:
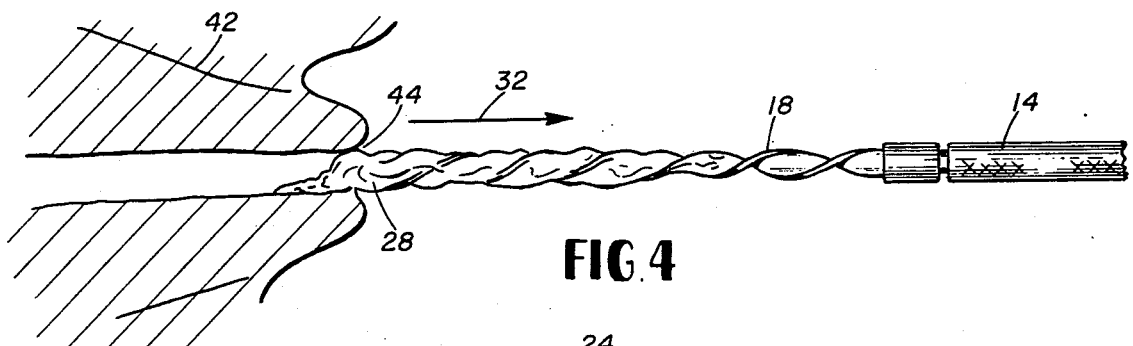
FIG. 4 is an elevation, in partial section, similar to FIG. 3, showing the wirthdrawal of the instrument from the endometrial cavity with a tissue-containing, mucous aggregate.

The rotating spiral section 18 presents a multiple of scraping surfaces to the tissue within the endometrial cavity. This enhances the purpose of gathering a cross section of tissue from essentially all portions of the cavity in a single manipulation of the medical instrument 10. Upon withdrawal of the sprial section 18, continued rotation in combination with the sharp (sharp relative to blunt edges) edges of the spiral section 18 results in the endometrial cells on the surface of the walls of the womb 42 being curetted, or scraped, therefrom and into the mucous aggregate 28. Since the spiral section 18 is formed with a matte surface, the mucous aggregate 28 will adhere more readily and effectively thereto. Referring to FIG. 4, the instrument 10 is moved in the direction of the arrow 32 to withdraw the mucous-containing spiral section 18 from the womb 42.

The mucous aggregate 28 is withdrawn with the spiral section 18 and provides in a simple, efficient and essentially painless manner, a cross section of endometrial tissue. Also some endocervical mucous is obtained upon withdrawal of the spiral section 18. This is accomplished by the unique design of the instrument 10 at the spiral section 18. The rotating of the instrument 10 permits essentially all areas of the wall of the womb 42 to be contacted with a complete cross section of endometrial tissue drawn onto the spiral section 18. As noted, the sharp edges of the spiral section draw those cells closest to the surface of the wall of the womb 42. Thus, the instrument 10 not only provides a complete cross section of all areas of the womb 42 but also draws from the complete depth of the mucous aggregate 28 to obtain endometrial tissue which is immediately adjacent to the wall of the womb.

The techniques illustrated in FIGS. 3 and 4, and with the use of the instrument 10, is simple and nearly painless and can be conducted as a routine, daily gynecological office procedure. This, of course, reduces the comparative costs.

The endometrial tissue obtained by use of the instrument 10 is free of any contaminants and is only supported by the inert plastic spiral section 18. At this point, the tissue-containing mucous aggregate 28 is ready for transfer to an examining media so that the tissue may be studied for hormone related capabilities of the patient or for diagnosing endometrial neoplasia. While some of the mucous aggregate 28 could be wiped from the spiral section 18 onto an examining surface, such as a slide, it is desirable to remove substantially all of the mucous aggregate from the spiral section to provide sufficient tissue for the diagnostic specimen and also for histological studies.

Figure 5:
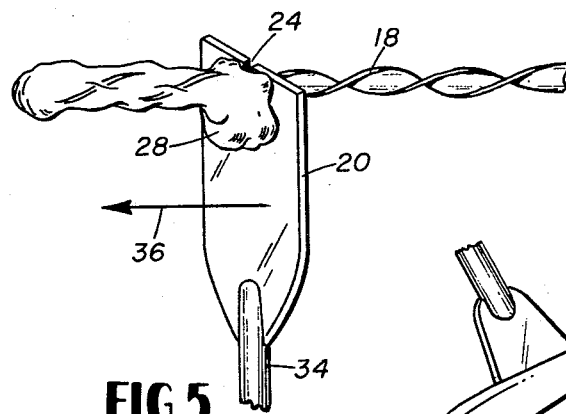
FIG. 5 is a perspective of a portion of the implement of FIG. 2 in temporary assembly with the tissue-containing spiral section of the instrument of FIG. 1 for the purpose of transferring the mucouse aggregate from the instrument to the implement.

To effect the efficient and essentially complete removal of the mucous aggregate 28 from the spiral section 18, the proximal portion of the spiral section is inserted into the slot 24 of the paddle 20 as shown in FIG. 5. The paddle 20 is moved slowly in the direction of the arrow 36, or the spiral section 18 is pulled slowly in the reverse direction, whereby the loosely held instrument 10 rotates. The rotation of the instrument 10 is caused by the spiral section 18 being forced through the slot 24. As the spiral section 18 moves through the slot 24, the mucous aggregate 28 is extruded, or wiped, from the spiral section and onto the paddle 20. The thin edges of the slot 24 provide a somewhat flexible wiper action which permits an essentially complete wiping of the mucous aggregate 28 from the spiral section 10. Subsequent to the removal of the mucous aggregate 28 from the spiral section 18, the relatively inexpensive section 18 is removed from the sleeve 14 and discarded.

Figure 6:
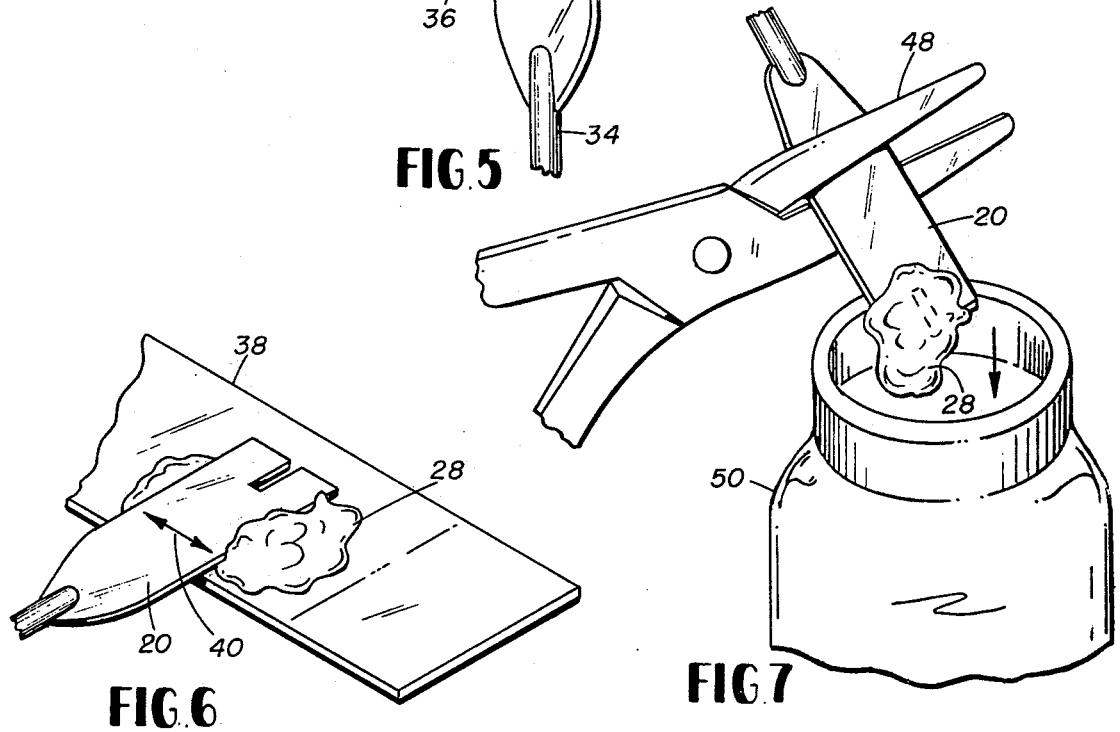
FIG. 6 is a perspective showing the transfer of the mucous aggregate from the implement of FIG. 2 to a slide.

Referring to FIG. 6, the paddle 20 is positioned to place the mucous aggregate 28 into engagement with a slide 38. Thereafter, the paddle 20 is moved back and forth as indicated by the arrows 40 to transfer an amount of the tissue-containing mucous aggregate 28 onto the slide 38 and spread the material evenly thereon.

The endometrial mucous is a thick, gliary, sticky substance and sometimes a swirling, or circular, motion of the paddle 20 is required to transfer the aggregate 28 evenly over the slide 38. The mucous aggregate 28 on the slide 38 should not be allowed to dry since drying results in a loss of significant cytological and nuclear detail. The slide 38 should be immediately placed in a jar containing a lysing agent so that any blood or debris which may be contained within the aggregate 28 is effectively cleared away. Thereafter, the slide 38 is removed from the lysing agent and placed in a container of 95% alcohol which serves as a fixative. Due to the thickness of the endometrial mucous aggregate 28, a fixative of 95% alcohol appears to be more effective than other available fixatives.

Figure 7:
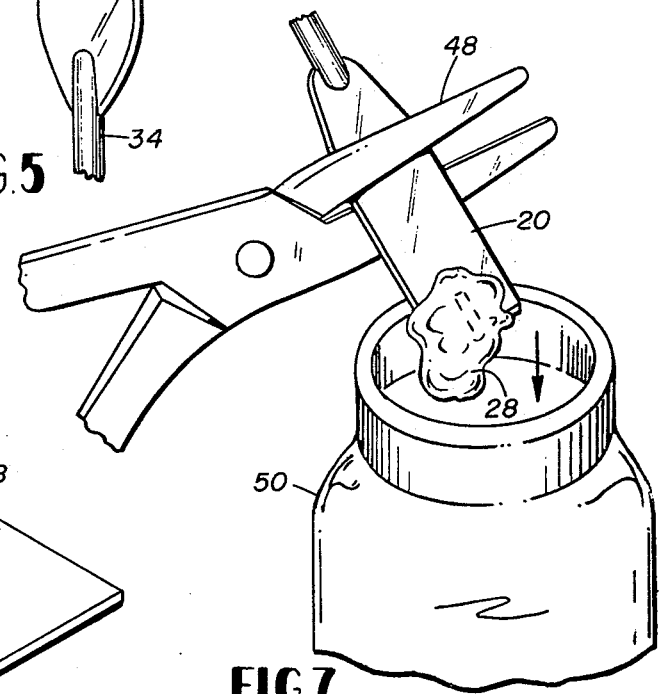
FIG. 7 is a perspective showing the depositing of the aggregate-supporting portion of the implement with the mucous aggregate into a container of 10% formalin.

As shown in FIG. 7, the remaining mucous aggregate 28 is gathered on the end of the paddle 20 which is then severed from the remaining portion thereof by the use of cutters 48. The severed, mucous-containing portion of the paddle 20 is dropped into a vial 50 containing 10% formalin. This remaining mucous aggregate 28 is usually sufficient for paraffin embedding and may be sufficiently large enough to provide enough tissue for a biopsy.

The spiral section 18 should be approximately 6 cm. in length while the most useful width is 3.5 mm. to 4.0 mm. The thickness of the spiral section 18 is about 0.75 mm. The diameter of the curved portion 22 and handle portion 34 of the implement 12 is about 3.5 mm. While these dimensions are representative of the disclosed embodiment, the invention may be practiced with many variations of dimensions to suit particular needs without departing from the spirit and scope of the invention.

Referring now to FIGS. 8 through 15, a tissue-gathering instrument 70 formed according to a second embodiment of the invention is shown. This embodiment of the invention is curved and has an inherent ductility, memory and springingness which permits adaptability to various curvatures and thus to the compound curves of the irregularly shaped endometrial cavity of a female. Although the instrument 10 was indicated as being potentially formable with a curved helical end-section, it is desired to particularly show an embodiment of the invention and to illustrate the manner of its use. The instrument 70 is similarly formed to the instrument 10 in that a handle 72 is present which terminates in a helix 74, the blade 74 being a flat, straight-sided (essentially a rectangular solid) member which is "twisted" about its longitudinal axis in a spiralling fashion to form the helical nature of the blade 74. Typically, the helix blade 74 is arcuate over its length, the body of the blade 74 curving away from the linear longitudinal axis of the handle 72 with a predetermined radius of curvature. In order to conform to the average uterine cavity, the blade 74 is shaped with a 3 inch radius of curvature. Thus, the blade 74 conforms to the axis of the uterus in relation to the vaginal canel, thereby aiding in insertion of the instrument 70 and reducing pain on insertion. The predetermined radius of curvature of the blade 74 also allows the tip of the blade 74 to circumscribe a circular or elliptical plane when rotated through 360°, in a manner to be more fully described hereinafter, within the endometrical or uterine cavity when the blade 74 is fully inserted and rotated within the cavity. Since the arcuate nature of the blade 74 conforms to the confines of the cavity, the entire surface area of the endometrium is contacted by the blade 74 on rotating of said blade within the uterine cavity. The blade 74 can be provided with a right-hand turn or with a left-hand turn to facilitate usage thereof.

The helix blade 74 is further seen in FIG. 9 to essentially be rectangular in cross-section, thus edges 76 of the blade 74 are 90° edges and provide a cutting edge which effectively scrapes or otherwise dislodges mucous and tissue from the walls of the endometrial cavity. The 90° edges 76 perform this function much more efficiently than can rounded or blunt edges. The blade 74 is also seen to have matte surfaces 78 over the surface faces thereof. The matte surfaces 78 may be molded or otherwise formed on the blade and result in the specimen adhering more readily to the blade.

The helix blade 74 is also seen to be formed with a rounded outer end portion which renders the insertion of the blade more comfortable and reduces the possibility of uterine perforation. The handle 72 and blade 74 can be formed unitarily of the same material, such as by molding. The material chosen should be resilient, spring, tough, pliable, and non-reactive to human secretions characteristics shared by a large number of plastic-type materials. The property of reliency allows the blade 74 to conform even better to the shape of the endometrial cavity. The material should be tough in order to allow the blade 74 to maintain its structural integrity while being rotated within the often heavily gelatinous environment of the cavity, thereby assuring proper removal of the gathered specimen. Further, these noted characteristics assure that the blade 74 does not break during the sampling procedure and also act to reduce the possibility of uterine perforation during the sampling procedure. The material chosen should also be biologically inert to prevent contamination of the sample or irritation of the walls of the uterine cavity. The material should also retain an inherent "memory" of original form so that this shape is regained after deformation of the blade.

Referring now to FIGS. 8 and 10, the blade 74 of the instrument 70 is seen at 80 in a "rest" position, i.e., the position occupied by the blade 74 when the instrument 70 is not being rotated. Rotation of the instrument 70 causes the blade 74 to "travel" in the planar arc represented by 82, it being understood that the arc 82 is an arc of rotation and that the blade 74 circumscribes a generally conical volume having its apex essentially at the juncture of the blade 74 and the handle 72. The tapering surfaces of this swept conical volume are slightly concave. The conical volume thus swept corresponds essentially the geometrical structure of the confines of the uterine cavity as seen in FIG. 10. Thus, insertion of the instrument 10 into the vagina 90, subsequently into the cervical opening 88 and into the endometrial cavity 86 and rotation of the instrument 10 therein causes contact of the edges 76 of the blade 74 with essentially the full surface area thereof. The arcuate blade 74, being also flexible and pliable, adapts its shape to the curvature of the cavity 86 so that the surface thereof is scraped by the edge 76 of the blade 74, the tissue and mucous specimen being "stored" within the volume defined by the spiral of the blade 74. This storing of the specimen within the spirals of the blade 74 prevents loss of the specimen and greatly aids in the gathering of a representative sampling of the entire cavity. Since the blade 74 gathers a full sampling of the surface layer of cells within the uterine cavity, small lesions and other potential or actual growths, etc., which may not be discovered with prior art sampling techniques are reliably found to contribute to the cell population of the sample, thereby insuring a more reliable diagnosis of potential disorders or other conditions, as seen in FIG. 11, a side cross-sectional view of the uterus, the blade 74 contacts all surfaces of the uterine cavity on rotation of the instrument 70.

Referring now to FIGS. 12 through 15, wherein rotation of the instrument 70 is noted by the numeral 92, a specimen 94 is shown, particular in FIG. 15, as it is being scraped from the walls of the cavity by the action of the blade 74. The specimen is seen at 96 to cling to the surfaces of the blade 74 in the manner previously described. Taking the position of one cross-sectional portion of the blade 74 to be at 98 when rotation of the instrument 70 is initiated, it is seen that the edges 76 scrape the walls of the cavity 84 to remove the surface layer cells, exfoliated cells and tissue fragments, and mucuous from the surfaces of the cavity on rotation of the blade 74. Taking successive cross-sections of the cavity 84 as shown in FIGS. 12, 13, and 14 respectively, the blade 74 is seen to circumscribe a progressively increasing conical volume as referred to herein above, the full surface area of cavity 84, which varies in diameter from a point near to cervix inwardly, is contacted by the blade 74. This full surface area is thereby scraped by the edges 76 of the blade 74 and the tissue sample is thereby gathered and held within the "flutes" of the spiralling helix blade 74 for removal from the cavity.

The specimen of tissue and mucuous is removed from the cavity by withdrawing the instrument 70, the specimen being removed from the blade 74 preferably by use of the implement 12 shown in FIG. 2. The use of the implement 12 is shown in FIGS. 5, 6, and 7. Since the utilization of the gathered specimen has previously been described, such description will not be repeated here.

It is to be particularly noted here that the present instrument, by virtue of the predetermined curvature of the blade 74 and the intrinsic "spring" of the material from which it is made, can adapt itself to the configuration of the uterine cavity in order to contact as much of the inner surface of the uterus as possible and to scrape off the superficial layer of the entire surface thereof. Th present device obtains a "homogenized" specimen from as much of the uterine surface as possible, thereby permitting an earlier discovery of extremerly small lesions which might otherwise go undetected.

Thus, the present medical instrument facilities an inventive and highly satisfactory method for obtaining direct smear tissues from endocervical and endometrial areas for the purpose of studying endometrial cytopathology. The use of this technique in comparison to other techniques, can be measured in the success of the adequacy of the endocervical and endometrial components, the quality of the slides and the clarity of cytoplasmic and nuclear detail. In addition, by using this technique, sufficient specimen is obtained to not only conduct the disagnostic tests but also for paraffin embedding and histological study. In some instances, enough additional specimen is obtained as biopsy material. All of these advantages are accomplished with a relatively simple, in-office, nearly painless procedure with the results being relatively quickly available and less costly.

Obviously many modifications and variations of the present invention are possible in light of the above teachings. It is, therefore, to be understood that within the scope of the appended claims the invention may be practiced otherwise than as specifically described.

What is claimed is:

1. A medical system for obtaining tissue samples for the endometrial cavity, comprising:

tissue gathering means including a helically-shaped end section, said end section being formed of a flat elongated and essentially rectangular member twisted about its longitudinal axis such that the edges thereof which extend in a direction parallel to the longitudinal axis of said member are disposed in a helically wound fashion about said longitudinal axis, the surface of the end section being of a matte finish to enhance the adhesion of tissue thereto, the end section being arcuately formed with a memoried curve therein and being formed of a flexible pliant material, the end section being curvilinear along the longitudinal axis of the aforesaid member, portions of the end section being adapted to engage the surfaces of the cavity to gather a cross-section of tissue from essentially all areas thereof;

handle means for manipulating said end section and being joined to the inner end portion of said end section, the handle means extending externally of the cavity on insertion of the end section thereinto for controlling the rotational movement of said end section within said cavity, the curvilinear longitudinal axis of the end section being skewed relative to the longitudinal axis of the handle means, the end section deflecting toward the walls of the cavity on insertion of said end section into said cavity whereby surfaces of the end section contact full surfaces of said walls; and a flat paddle-shaped member having a slot-like opening formed therein, at least a portion of the helically shaped end section of the tissue gathering means being disposed within the slot-like opening and being movable relative thereto to transfer tissue adhering to the end section from said end section to a surface of the flat paddle-shaped member.

2. The medical system of claim 1 wherein the handle means comprises a rod-like handle member connected to the inner end portion of said end section, the handle member being rotatable to cause the end section to circumscribe a substantially conical volume to facilitate contact of the end section with the walls of the cavity.

3. The medical system of claim 1 wherein the end section is formed with a predetermined radius of curvature, the radius of curvature of the end section being defined as the radius of the circular arc along which the end section lies, rotation of the end section causing the end section to circumscribe a generally conical volume corresponding to the volumetric dimensions of the cavity.

4. The medical system of claim 3 wherein the end section has a three-inch radius of curvature.

5. The medical system of claim 1, wherein said opening is a slot having opposed side walls spaced apart a distance equal to at least the thickness of the edges of the end section.

6. The medical system of claim 5 wherein the slot is formed in one edge of the member, the helically shaped end section being disposed within the slot at the inner end of said section, the body portion of the end section being drawn toward the member to transfer tissue on said section onto that surface of the member opposite the direction of motion of the end section, the side walls of the slot acting to deposit the tissue on the member.

7. The medical system of claim 1 wherein the opening is defined by side walls of a reduced thickness relative to the remaining portions of the member, the side walls being flexible to provide a wiping action against surfaces of the end section moving relatively thereto to facilitate transfer of tissue on the end section from said end section to said member.

8. The medical system of claim 1, wherein the surfaces of the end section have a roughened finish to enhance adhesion of the gathered tissue thereto.

9. The medical system of claim 1 wherein the surfaces of the end section intersect at an angle of 90° to form relatively sharp edges, which edges contact the surfaces of the cavity to scrape tissue-bearing material therefrom.

10. The medical system of claim 1 wherein the end section is formed with a rounded outer end portion to facilitate insertion of the apparatus into the body cavity.

* * * * *